United States Patent
Cho

(10) Patent No.: US 11,371,020 B2
(45) Date of Patent: Jun. 28, 2022

(54) USES OF EPITHELIAL-TO-MESENCHYMAL INHIBITORS IN GENERATING PACEMAKER CELLS

(71) Applicants: Emory University, Atlanta, GA (US); Children's Healthcare of Atlanta, Inc., Atlanta, GA (US)

(72) Inventor: Hee Cheol Cho, Johns Creek, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 450 days.

(21) Appl. No.: 16/098,560

(22) PCT Filed: May 2, 2017

(86) PCT No.: PCT/US2017/030659
§ 371 (c)(1),
(2) Date: Nov. 2, 2018

(87) PCT Pub. No.: WO2017/192602
PCT Pub. Date: Nov. 9, 2017

(65) Prior Publication Data
US 2019/0144829 A1    May 16, 2019

Related U.S. Application Data

(60) Provisional application No. 62/420,710, filed on Nov. 11, 2016, provisional application No. 62/330,489, filed on May 2, 2016.

(51) Int. Cl.
*C12N 5/077* (2010.01)
*A61P 9/06* (2006.01)
*A61K 35/34* (2015.01)
*A61K 31/4709* (2006.01)
*A61K 35/28* (2015.01)
*A61K 36/9066* (2006.01)
*A61K 31/7088* (2006.01)
*A61K 45/06* (2006.01)

(52) U.S. Cl.
CPC ........ *C12N 5/0657* (2013.01); *A61K 31/4709* (2013.01); *A61K 31/7088* (2013.01); *A61K 35/28* (2013.01); *A61K 35/34* (2013.01); *A61K 36/9066* (2013.01); *A61K 45/06* (2013.01); *A61P 9/06* (2018.01); *C12N 2501/60* (2013.01); *C12N 2501/999* (2013.01); *C12N 2506/1315* (2013.01)

(58) Field of Classification Search
CPC ................................ C12N 5/0657; A61P 9/06
See application file for complete search history.

(56) References Cited

U.S. PATENT DOCUMENTS

| | | |
|---|---|---|
| 6,690,970 B1 | 2/2004 | Taheri |
| 9,763,999 B2 | 9/2017 | Marban |
| 2003/0211088 A1 | 11/2003 | Field |
| 2004/0254134 A1 | 12/2004 | Marban |
| 2013/0189780 A1* | 7/2013 | Shoemaker .......... C12N 5/0696 435/375 |
| 2015/0359845 A1 | 12/2015 | Marban |

FOREIGN PATENT DOCUMENTS

| WO | 2001068814 | 9/2001 |
|---|---|---|
| WO | 2015173425 | 11/2015 |

OTHER PUBLICATIONS

Beauchamp et al. Development and Characterization of a Scaffold-Free 3D Spheroid Model of Induced Pluripotent Stem Cell-Derived Human Cardiomyocytes, Tissue Engineering Part C 21(8): 852-861 (Year: 2015).*
Komori. Regulation of Osteoblast Differentiation by Transcription Factors, 2006, Journal of Cellular Biochemistry 99:1233-1239 (Year: 2006).*
McNally et al. Setting the Pace Tbx3 and Tbx18 in Cardiac Conduction System Development Circ Res. 2009 104:285-287 (Year: 2009).*
Toden et al. Curcumin mediates chemosensitization to 5-fluorouracil through miRNA-induced suppression of epithelialto-mesenchymal transition in chemoresistant colorectal cancer Carcinogenesis, 2015, vol. 36, No. 3, 355-367 (Year: 2015).*
Vasquez-Martin Metformin regulates breast cancer stem cell ontogeny by transcriptional regulation of the epithelial-mesenchymal transition (EMT) status 2010 Cell Cycle 9:18, 3807-3814 (Year: 2010).*
Meidhof et al. ZEB1-associated drug resistance in cancer cells isreversed by the class I HDAC inhibitor mocetinostat EMBO Mol Med (2015) 7: 831-847 (Year: 2015).*
Low Telomerase: central regulator of all of the hallmarks of cancer 2013. Trends in Biochemical Sciences vol. 38, No. 9: 426-434). (Year: 2013).*
Wang, Evodiamine induces apotosis and inhibits self-renewal of gastric cancer stem cells through the Wnt/β-catenin signaling pathway 2014—cpfd.cnki.com.cn (Year: 2014).*
Tania, Epithelial to mesenchymal transition inducing transcription factors and metastatic cancer Tumor Biol. (2014) 35:7335-7342 (Year: 2014).*
Rocca et al. Palbociclib (PD 0332991): targeting the cell cycle machinery in breast cancer, Expert Opinion on Pharmacotherapy, 2014, 15:3, 407-420 (Year: 2014).*

(Continued)

*Primary Examiner* — Taeyoon Kim
*Assistant Examiner* — Alexandra F Connors
(74) *Attorney, Agent, or Firm* — Emory Patent Group

(57) ABSTRACT

This disclosure relates to methods of generating pacemaker cells for use in therapeutic strategies that address a heart that beats abnormally. In certain embodiments, one mixes cells with an epithelial-to-mesenchymal transformation inhibitor in combination with a nucleic acid encoding a transcription factor such as a vector that encodes a transcription factor such as Tbx18 in operable combination with a eukaryotic promoter to produce pacemaker cells that are then transplanted into the heart.

8 Claims, 6 Drawing Sheets

(56) References Cited

OTHER PUBLICATIONS

Sun et al. Intratumoral Hepatic Stellate Cells as a Poor Prognostic Marker and a New Treatment Target for Hepatocellular Carcinoma 2013 PLoS ONE 8(11): e80212 (Year: 2013).*
Liu et al. Liposome encapsulated Disulfiram inhibits NFκB pathway and targets breast cancer stem cells in vitro and in vivo 2014 Oncotarget (17): 7471-7485 (Year: 2014).*
Huber et al. NF-κB is essential for epithelial-mesenchymal transition and metastasis in a model of breast cancer progression J Clin Invest. 2004;114(4):569-581 (Year: 2004).*
Prasannan et al. Key cell signaling pathways modulated by zerumbone: Role in the prevention and treatment of cancer Biochemical Pharmacology 84 (2012) 1268-1276 (Year: 2012).*
Qiu et al. Bufalin, a component in Chansu, inhibits proliferation and invasion of hepatocellular carcinoma cells BMC Complementary and Alternative Medicine 2013, 13:185 (Year: 2013).*
Kutuk et al. Aspirin inhibits TNFa- and IL-1-induced NF-kB activation and sensitizes HeLa cells to apoptosis Cytokine 25 (2004) 229e237 (Year: 2004).*
Barbuti et al. Stem Cell-Derived Nodal-Like Cardiomyocytes as a Novel Pharmacologic Tool: Insights from Sinoatrial Node Development and Function, Pharmacol Rev 67:368-388, 2015.
Garamszegi et al. Crosstalk Signalling Role in Modulation of Drugs Side Effects, Current Molecular Pharmacology, 2012, 5, 327-339.
Hashem et al. Genetic isolation of stem cell-derived pacemaker-nodal cardiac myocytes, Mol Cell Biochem (2013) 383:161-171.
Hu et al. Biological pacemaker created by minimally invasive somatic reprogramming in pigs with complete heart block, Sci Transl Med, 2014, 6(245):245ra94.
Husse et al. Generation of cardiac pacemaker cells by programming and differentiation, Biochimica et Biophysica Acta 1863 (2016) 1948-1952.
Ionta et al. SHOX2 Overexpression Favors Differentiation of Embryonic Stem Cells into Cardiac Pacemaker Cells, Improving Biological Pacing Ability, Stem Cell Reports, vol. 4, 129-142, 2015.
Jung et al., Programming and Isolation of Highly Pure Physiologically and Pharmacologically Functional Sinus-Nodal Bodies from Pluripotent Stem Cells, Stem Cell Reports, vol. 2, 592-605, 2014.
Kapoor et al. Direct conversion of quiescent cardiomyocytes to pacemaker cells by expression of Tbx18, Nat Biotechnol, 2013, 31(1):54-62.
Protze et al. Sinoatrial node cardiomyocytes derived from human pluripotent cells function as a biological pacemaker, Nat Biotechnol, 2017, 35(1):56-68.
Rimmbach et al. Generation of Murine Cardiac Pacemaker Cell Aggregates Based on ES-Cell-Programming in Combination with Myh6-Promoter-Selection, J. Vis. Exp. (96), e52465 (2015).
Ruhparwar et al. Enrichment of cardiac pacemaker-like cells: neuregulin-1 and cyclic AMP increase I-current density and connexin40 mRNA levels in fetal cardiomyocytes, Med Bio Eng Comput (2007) 45:221-227.
Saito et al. Enhancement of Spontaneous Activity by HCN4 Overexpression in Mouse Embryonic Stem Cell-Derived Cardiomyocytes—A Possible Biological Pacemaker, PLoS ONE 10(9): e0138193, 2015.
Scavone et al. Embryonic Stem Cell-Derived CD166+ Precursors Develop Into Fully Functional Sinoatrial-Like Cells, Circ Res 2013;113:389-398.
Tojo et al. The ALK-5 inhibitor A-83-01 inhibits Smad signaling and epithelial-to-mesenchymal transition by transforming growth factor-β, Cancer Sci 2005, 96: 791-800.
Xiao et al. Cellular Reprogramming Approaches to Engineer Cardiac Pacemakers, Current Cardiology Reports (2020) 22: 29.
Beauchamp et al. Development and Characterization of a Scaffold-Free 3D Spheroid Model of Induced Pluripotent Stem Cell-Derived Human Cardiomyocytes, TISSUE ENGINEERING: Part C, 2015, vol. 21, 852.
Komori, Regulation of Osteoblast Differentiation by Transcription Factors, J. Cell. Biochem, 99: 1233-1239, 2006.
Lee et al., Promoter-specific lentivectors for long-term, cardiac-directed therapy of Fabry disease, Journal of Cardiology (2011) 57, 115-122.
Mckinlay et al. Charge-altering releasable transporters (CARTs) for the delivery and release of mRNA in living animals, PNAS, 2017 114 4) E448-E456.
Sahin et al. mRNA-based therapeutics—developing a new class of drugs, Nat Rev Drug Discov, 2014, 13(10):759-80.
Takeichi et al., The Transcription Factors Tbx18 and Wt1 Control the Epicardial Epithelial-Mesenchymal Transition through Bi-Directional Regulation of Slug in Murine Primary Epicardial Cells, PLoS ONE, 2013, 8(2): e57829.

* cited by examiner

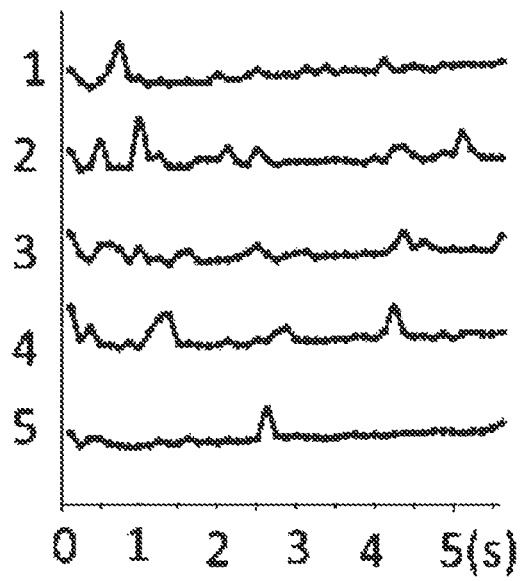
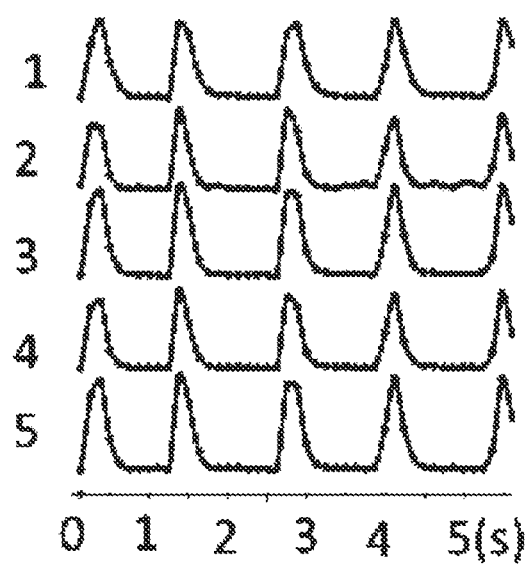
FIG. 5A
FIG. 5B
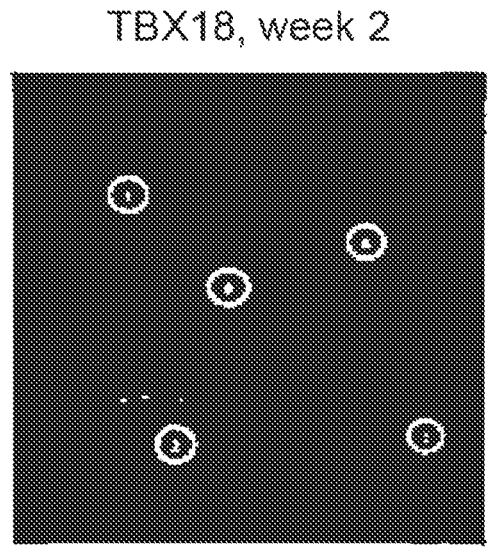
FIG. 6A
FIG. 6B

USES OF EPITHELIAL-TO-MESENCHYMAL INHIBITORS IN GENERATING PACEMAKER CELLS

CROSS-REFERENCE TO RELATED APPLICATIONS

This application is the National Stage of International Application No. PCT/US2017/030659 filed May 2, 2017, which claims the benefit of U.S. Provisional Application No. 62/330,489 filed May 2, 2016 and U.S. Provisional Application No. 62/420,710 filed Nov. 11, 2016. The entirety of each of these applications is hereby incorporated by reference for all purposes.

STATEMENT REGARDING FEDERALLY FUNDED RESEARCH

This invention was made with government support under 5R01 HL 111646-05 awarded by the National Institutes of Health. The government has certain rights in the invention.

BACKGROUND

When healthy, every heartbeat originates from native pacemaker cells, and the vast majority of the heart cells have no ability to pace. Cardiac arrhythmia, also known as bradyarrhythmia or bradycardia, is a slow heart rate. Cardiac arrhythmia can be a result of dysfunctional pacemaker cells in the sinoatrial node (SA node) or the atrioventricular node (AV node). The main treatment for cardiac arrhythmia is usually an implanted device that generates electrical impulses to regulate the heartbeat, a permanent pacemaker. There are significant problems with electronic pacing devices as it requires repeated surgical procedures to replace batteries; lead wires can be dislodged or broken, which results in aberrant electrical shocks or no pacing; and infection in either the generator or the leads requires complete removal of all hardware. Thus, there is a need to identify improved treatment approaches.

Kapoor et al. report direct conversion of quiescent cardiomyocytes to pacemaker cells by expression of Tbx18. Nat Biotechnol. 2013, 31(1):54-62. See also US20150359845; Cho, Curr Cardiol Rep. 2015, 17(8):65; Hu et al. Science Translational Medicine, 2014, 6, 245: 245ra94; Yang et al. Int J Mol Med. 2016, 38(5):1403-1410.

Tojo et al. report the ALK-5 inhibitor A-83-01 inhibits Smad signaling and epithelial-to-mesenchymal transition by transforming growth factor-beta. Cancer Sci. 2005, 96(11): 791-800. See also Zhu et al. Cell Stem Cell. 2010, 7:651-655.

References cited herein are not an admission of prior art.

SUMMARY

This disclosure relates to methods of generating pacemaker cells for use in therapeutic strategies that address a heart that beats abnormally. In certain embodiments, one mixes cells with an epithelial-to-mesenchymal transformation inhibitor in combination with a nucleic acid encoding a transcription factor such as a vector that encodes a transcription factor such as Tbx18 in operable combination with a eukaryotic promoter to produce pacemaker cells that are then transplanted into the heart.

In certain embodiments, cells proliferate in a hanging droplet to form a spheroidal-like aggregate of spontaneously beating expanded cells. In certain embodiments, this disclosure contemplates alternative methods that create spheroid aggregates such as low-attachment plates and use of agarose-coated plates on which cells form spontaneously aggregates.

In certain embodiments, this disclosure relates to methods of treating or preventing a heart from beating abnormally comprising administering an effective amount of an epithelial-to-mesenchymal transformation inhibitor to a subject in need thereof. In certain embodiments, this disclosure relates to methods of treating or preventing an abnormally slow heart rhythm by administering an effective amount an epithelial-to-mesenchymal transformation inhibitor in combination with one or more transcription factors or a nucleic acid encoding a transcription factor such as a recombinant vector that encodes a transcription factor such at Tbx18 in operable combination with a eukaryotic promoter to a subject in need thereof.

In certain embodiments, this disclosure relates to compositions comprising: a) an epithelial-to-mesenchymal transformation inhibitor, and b) a transcription factor, a nucleic acid encoding a transcription factor such as a recombinant vector encoding a transcription factor operably linked to a eukaryotic promoter, or a combination thereof. In certain embodiments, the epithelial-to-mesenchymal transformation inhibitor blocks phosphorylation of Smad2 to inhibit TGF-β-induced epithelial-to-mesenchymal transition. In certain embodiments, the epithelial-to-mesenchymal transformation inhibitor is 3-(6-methyl-2-pyridinyl)-N-phenyl-4-(4-quinolinyl)-1H-pyrazole-1-carbothioamide or salts thereof. In certain embodiments, the transcription factor is Tbx18, Shox2, Tbx3, Tbx5, or combinations thereof. In certain embodiments, the composition further comprises a cell. In certain embodiments, the cell is a cardiac myocyte, a ventricular myocyte, atrial myocyte, nodal myocyte, or a stem cell. In certain embodiments, the stem cell is an embryonic stem cell, pluripotent stem cell, mesenchymal stromal cell, mesenchymal stem cell, adipose tissue-derived multipotent stem cell, or an induced cardiac-like cell derived therefrom a stem cell. In certain embodiments, the cell is a eukaryotic cell, mammalian cell, or human cell.

In certain embodiments, the epithelial-to-mesenchymal transformation inhibitor is 3-(6-methyl-2-pyridinyl)-N-phenyl-4-(4-quinolinyl)-1H-pyrazole-1-carbothioamide, aspirin (acetylsalicylic acid), curcumin, mocetinostat, zidovudine, evodiamine, pyrinium, pyrvinium pamoate, moscatilin, metformin, palbociclib, icaritin, disulfiram, zerumbone, bufalin, salts, derivatives, or combinations thereof.

In certain embodiments, this disclosure relates to methods of generating cells that spontaneously beat comprising mixing cells with a) an epithelial-to-mesenchymal transformation inhibitor, and b) a transcription factor, a nucleic acid encoding a transcription factor such as a recombinant vector encoding a transcription factor operably linked to a eukaryotic promoter, or combination thereof; wherein mixing is under conditions such that the cells proliferate providing spontaneously beating expanded cells.

In certain embodiments, this disclosure relates to methods of treating or preventing a heart from beating abnormally comprising implanting an effective amount of spontaneously beating expanded cells into the heart of a subject in need thereof, wherein the spontaneously beating expanded cells are made by a process comprising mixing cells with a) an epithelial-to-mesenchymal transformation inhibitor, and b) a transcription factor, a nucleic acid encoding a transcription factor such as a recombinant vector encoding a transcription factor operably linked to a eukaryotic promoter, or combination thereof; wherein mixing is under conditions such that the cells proliferate providing spontaneously beating expanded cells.

In certain embodiments, the subject is diagnosed with cardiac arrhythmia, sick sinus syndrome, sinus bradycardia, tachycardia-bradycardia syndrome, atrial fibrillation, atrioventricular block, chronotropic incompetence, prolonged QT syndrome, or heart failure. In certain embodiments, the epithelial-to-mesenchymal transformation inhibitor is 3-(6-methyl-2-pyridinyl)-N-phenyl-4-(4-quinolinyl)-1H-pyrazole-1-carbothioamide, or salts thereof, and the transcription factor is Tbx18, Shox2, Tbx3, Tbx5, or combinations thereof.

In certain embodiments, the disclosure relates to a pharmaceutical composition comprising an epithelial-to-mesenchymal transformation inhibitor disclosed herein, 3-(6-methyl-2-pyridinyl)-N-phenyl-4-(4-quinolinyl)-1H-pyrazole-1-carbothioamide or salts thereof and a pharmaceutically acceptable excipient. In certain embodiments, the composition further comprises one or more transcription factors or a nucleic acid encoding a transcription factor such as a recombinant vector that encodes a transcription factor in operable combination with a eukaryotic promoter.

In certain embodiments, the disclosure relates to methods of generating a biological pacemaker using an epithelial-to-mesenchymal transformation inhibitor and transcription factors to modify the electrical activity of the cardiac tissue of a subject comprising: identifying a subject having cardiac tissue exhibiting abnormal electrical activity, wherein said subject has cardiac tissue comprising quiescent cells, wherein the quiescent cells comprise one or more of cardiomyocytes and stem cells, and administering one or more transcription factors or nucleic acid encoding a transcription factor to said quiescent cells to generate treated cells, wherein the treated cells exhibit spontaneous, repetitive electrical activity or an increased pace, intensity, or consistency of spontaneous, repetitive electrical activity, thereby modifying electrical activity of the cardiac tissue said subject.

In certain embodiments, the subject is afflicted with a condition selected from the group consisting of sick sinus syndrome, sinus bradycardia, tachycardia-bradycardia syndrome, atrial fibrillation, atrioventricular block, chronotropic incompetence, prolonged QT syndrome, and heart failure. In certain embodiments, the abnormal cardiac electrical activity is due to a cardiac arrhythmia.

In certain embodiments, the methods disclosed herein comprises administering cells pre-treated with an epithelial-to-mesenchymal transformation inhibitor in combination with one or more transcription factors or a nucleic acid encoding a transcription factor such as a recombinant vector encoding a transcription factor to said subject. In certain embodiments, the administration occurs in vivo. In certain embodiments, the administration is to a site selected from the group consisting of the apex of the heart, right branch of the Bundle of His, the left branch of the Bundle of His, the Purkinje fibers, the inter-ventricular septum, the right ventricular free wall, the left ventricular free wall, the SA node, the AV node. In certain embodiments, the administration site is accessed via the right ventricle. In certain embodiments, the administration site is accessed via the right atrium. In certain embodiments, the administration site is accessed by accessing the heart directly. In certain embodiments, the access is achieved by a map guided catheter injection system. In certain embodiments, the access is achieved by fluoroscopy guidance. In certain embodiments, the access is achieved by X-ray guidance. In certain embodiments, the access is achieved by echocardiography guidance. In certain embodiments, the access is achieved by guidance via magnetic resonance imaging.

In certain embodiments, the administration comprises delivering one or more transcription factors or a nucleic acid encoding a transcription factor such as a recombinant vector to a site selected from the group consisting of the apex of the heart, right branch of the Bundle of His, the left branch of the Bundle of His, the Purkinje fibers, the inter-ventricular septum, the right ventricular free wall, the left ventricular free wall, the SA node, the AV node. In certain embodiments, the recombinant vector is a viral vector of non-viral vector. In certain embodiments, the method further comprises administering an epithelial-to-mesenchymal transformation inhibitor disclosed herein before, during, or after delivering the one or more transcription factors or nucleic acid encoding a transcription factor or recombinant vector. In certain embodiments, administration is oral, intravenous, or by direct injection into the heart or peritoneal cavity.

In certain embodiments, the nucleic acid or recombinant vector comprises one or more viral nucleic acid sequences. In certain embodiments, the viral vector is selected from the group consisting of adenovirus, adeno-associated virus, lentivirus, retrovirus, HJV, HIV, and HSV. Wherein the vector comprises one or more genes that encode a protein expressed by adenovirus, adeno-associated virus, lentivirus, retrovirus, HJV, HIV, and HSV. In certain embodiments, the non-viral vector is one or more of the following: plasmid, liposomal vectors, a cationic polymers, and/or DNA binding polymers. In certain embodiments, the recombinant vector is DNA or RNA optionally having a regulatory element.

In certain embodiments, the treated cells exhibit a length-to-width morphology substantially similar to a length-to-width morphology of native SAN cells. In certain embodiments, the treated cells have a length-to-width ratio of at least about 10. In certain embodiments, the treated cells exhibit an increase in spontaneous intracellular $Ca^{2+}$ oscillations. In certain embodiments, the spontaneous, repetitive electrical activity increases in response to beta-adrenergic stimulation. In certain embodiments, the converted cells do not express atrial natriuretic peptide (ANP) or skeletal alpha-actin (alphaSkA).

In certain embodiments, the subject has an electronic pacemaker to modify the electrical activity of the cardiac tissue. In certain embodiments, the generation of the biological pacemaker supplements the function of the electronic pacemaker. In certain embodiments, the generation of the biological pacemaker functionally replaces the electronic pacemaker.

In certain embodiments, this disclosure relates to methods of generating a biological pacemaker using an epithelial-to-mesenchymal transformation inhibitor and transcription factors or a nucleic acid encoding a transcription factor to treat an abnormally beating heart or cardiac arrythmia comprising: identifying a subject suffering from an abnormally beating heart cardiac arrhythmia, wherein said subject has cardiac tissue comprising quiescent cells, wherein the quiescent cells comprise one or more of cardiomyocytes and stem cells, wherein the quiescent cells exhibit do or do not exhibit spontaneous, repetitive electrical activity or beat abnormally; and administering an epithelial-to-mesenchymal transformation inhibitor and one or more transcription factors, nucleic acid, or recombinant vector encoding such to said quiescent cells to generate treated cells, wherein the treated cells exhibit increased consistency or increased pace or increased intensity of spontaneous, repetitive electrical activity; thereby treating said abnormally beating heart or cardiac arrhythmia.

In certain embodiments, this disclosure relates to methods of converting a population of stem cells through the use of an epithelial-to-mesenchymal transformation inhibitor and transcription factors into cells suitable for generation of a biological pacemaker, comprising: obtaining a population of stem cells; culturing said stem cells in vitro; wherein said cultured stem cells comprise quiescent cells that do or do not exhibit spontaneous, repetitive electrical activity; delivering one or more transcription factors in combination with an epithelial-to-mesenchymal transformation inhibitor or nucleic acid encoding the same to said quiescent cells to generate converted cells, wherein the converted cells exhibit spontaneous, repetitive electrical activity; thereby converting said stem cells into cells capable of generating a biological pacemaker.

In certain embodiments, one or more transcription factors are regulators of embryonic sinoatrial node development and/or promote de novo cellular differentiation into sinoatrial nodal cells. In certain embodiments, one or more transcription factors define the sinus venosus during development. In certain embodiments, one or more transcription factors are negative regulators of Nkx2.5 in the sinus venosus. In certain embodiments, the one or more transcription factors is selected from the group consisting of Tbx18, Shox-2, Tbx3, Tbx5, functional fragments thereof, and combinations thereof. In certain embodiments, one or more transcription factors comprises Tbx18. In certain embodiments, one or more transcription factors comprises Shox-2.

In certain embodiments, this disclosure relates to method of treating a dysfunction in cardiac electrical activity comprising: obtaining cells converted as described herein and administering said converted cells to a subject suffering from a dysfunction in cardiac electrical activity, wherein said converted cells exhibit spontaneous, repetitive electrical activity, thereby treating said dysfunction in cardiac electrical activity. In certain embodiments, the method further comprises administering an epithelial-to-mesenchymal transformation inhibitor to the subject.

In certain embodiments the methods further comprises isolating said converted cells prior to said administration. In certain embodiments, the spontaneous, repetitive electrical activity is within about 65% to about 100% of the normal activity of pacemaker cells. In certain embodiments, the administration causes a change in the rhythm of the heart. In certain embodiments, the changed rhythm of the heart corresponds to a new heart rate within about 25% to about 35% of a normal heart rate. In certain embodiments, administration is to a subject having an implanted pacemaker.

In certain embodiments, administration reduces the dependence of said subject on said implanted pacemaker. In certain embodiments, the reduced dependence is sufficient to allow explanting or replacement of said implanted pacemaker.

In certain embodiments, administration is into the apex of the heart, to the right branch of to the SA node, to the AV node, to the Bundle of His, to the left branch of the Bundle of His, to the Purkinje fibers, the inter-ventricular septum, to the right ventricular free wall, to the left ventricular free wall, via the right ventricle, via the right atrium In certain embodiments, this disclosure relates to compositions for the generation of a biological pacemaker comprising: an epithelial-to-mesenchymal transformation inhibitor and a nucleic acid encoding a transcription factor such as a recombinant vector, said system comprising: a viral vector encoding Tbx18, Shox-2, Tbx3, Tbx5, functional fragments thereof, or combinations thereof in operable combination with a eukaryotic promoter.

In certain embodiments, the viral vector is an adenoviral vector or lentiviral vector. In certain embodiments, the vector further comprises the following operably linked components in sequence: a first inverted terminal repeat sequence (ITR); a first lox P site; a packaging site; a cytomeglovirus promoter; a sequence encoding Tbx18, Shox2, or combinations thereof; an internal ribosome entry site (IRES); a polyadenylation signal (An); a second lox P site; a sequence encoding the adenovirus early region 2 and early region 4 genes; and a second inverted repeat sequence (ITR).

In certain embodiments, the disclosure relates to a population of cells for the generation of a biological pacemaker comprising: a plurality of stem cells, wherein the stem cells have been contacted with an epithelial-to-mesenchymal transformation inhibitor in combination with one or more transcription factors or nucleic acid encoding the same selected from the group consisting of Tbx18, Shox-2, Tbx3, Tbx5, functional fragments thereof, and combinations thereof, wherein said one or more transcription factors or nucleic acid induce an increase in the spontaneous, repetitive electrical activity of said cells, wherein said increase in the spontaneous, repetitive electrical activity of said cells is capable of generating an ectopic contraction of said cells, and wherein said stem cells are suitable for administration to a subject in need of biological pacemaker function.

In certain embodiments, the stem cells are selected from the group consisting of embryonic stem cells, non-embryonic stem cells, bone marrow-derived stem cells, adipose-derived stem cells, induced pluripotent stem cells, and cardiac stem cells.

In certain embodiments, this disclosure relates to the use of an epithelial-to-mesenchymal transformation inhibitor in combination with one or more transcription factors or nucleic acid encoding the same selected from the group consisting of Tbx18, Shox-2, Tbx3, Tbx5, functional fragments thereof, and combinations thereof to convert quiescent cells that do not exhibit spontaneous, repetitive electrical activity into pacemaker cells that exhibit spontaneous, repetitive electrical activity.

In certain embodiments, this disclosure relates to methods of treating a cardiac arrhythmia using transcription factors comprising: identifying a subject suffering from cardiac arrhythmia, wherein said subject has cardiac tissue comprising quiescent cells, wherein the quiescent cells comprise one or more of cardiomyocytes and stem cells, wherein the quiescent cells do not exhibit spontaneous, repetitive electrical activity or do not exhibit sufficient spontaneous, repetitive electrical activity or exhibit abnormally slow spontaneous, repetitive electrical activity; and administering an epithelial-to-mesenchymal transformation inhibitor in combination with one or more of Tbx18, Shox-2, Tbx3, Tbx5, functional fragments thereof, or combinations thereof or nucleic acid encoding the same, to said quiescent cells to generate treated cells, wherein the treated cells exhibit increased spontaneous, repetitive electrical activity; thereby treating said cardiac arrhythmia.

In certain embodiments, this disclosure relates to method of treating a cardiac arrhythmia by generating a biological pacemaker using an epithelial-to-mesenchymal transformation inhibitor and transcription factors, comprising: identifying a subject suffering from cardiac arrhythmia; obtaining a population of converted stem cells, wherein, prior to said conversion, said stem cells comprised quiescent cells that did not exhibit spontaneous, repetitive electrical activity; wherein an epithelial-to-mesenchymal transformation inhibitor and one or more of Tbx18, Shox-2, Tbx3, Tbx5, functional fragments thereof, or combinations thereof or nucleic acid encoding the same were administered to said quiescent cells to generate converted cells that exhibit spontaneous, repetitive electrical activity; and administering said converted cells to said subject, wherein said administered converted cells engraft into the cardiac tissue of said subject and continue to exhibit spontaneous, repetitive electrical activity, thereby generating a biological pacemaker and treating said cardiac arrhythmia.

BRIEF DESCRIPTION OF THE DRAWINGS

FIG. 5A shows TBX18-iPCs Ca2+ transients recording with Cal590 after two weeks.

FIG. 5B shows TBX18-iPCs exhibit synchronous and rhythmic pacing upon EMT inhibition indicating EMT blockade creates synchronous and rhythmic pacing from TBX18-iPCs, similar to the native SAN.

FIG. 6A shows a picture and location of the recordings in FIG. 5A.

FIG. 6B shows a picture and location of the recordings in FIG. 5B resembling that of the native sinoatrial node tissue after two weeks.

DETAILED DISCUSSION

Figure 1:
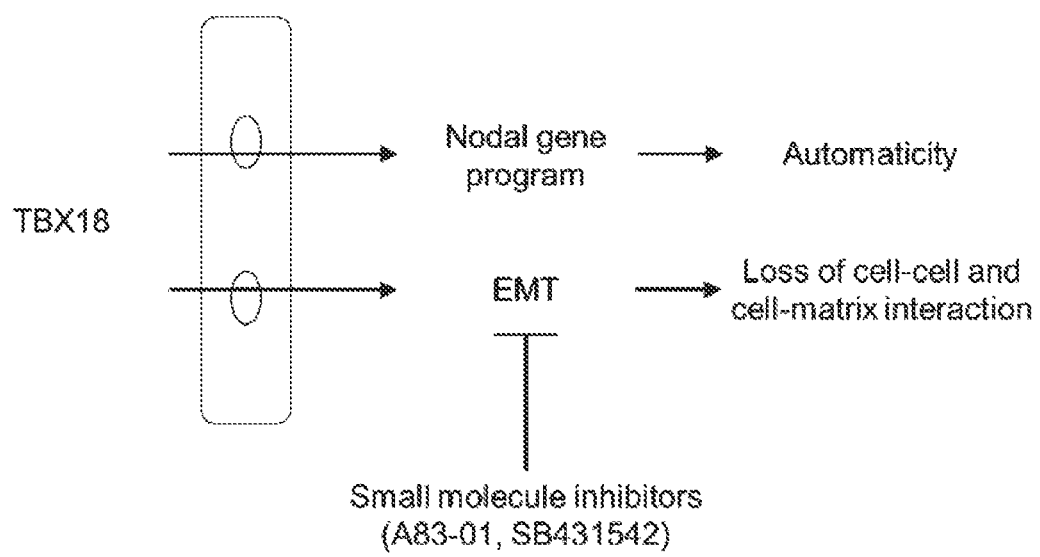
FIG. 1 illustrates that TBX18-induced pacemaker cells (TBX18-iPCs) migrate, and inhibition of EMT in TBX18-iPCs can stop or slow the migration, thereby enhancing its pacing function.
Figure 2:
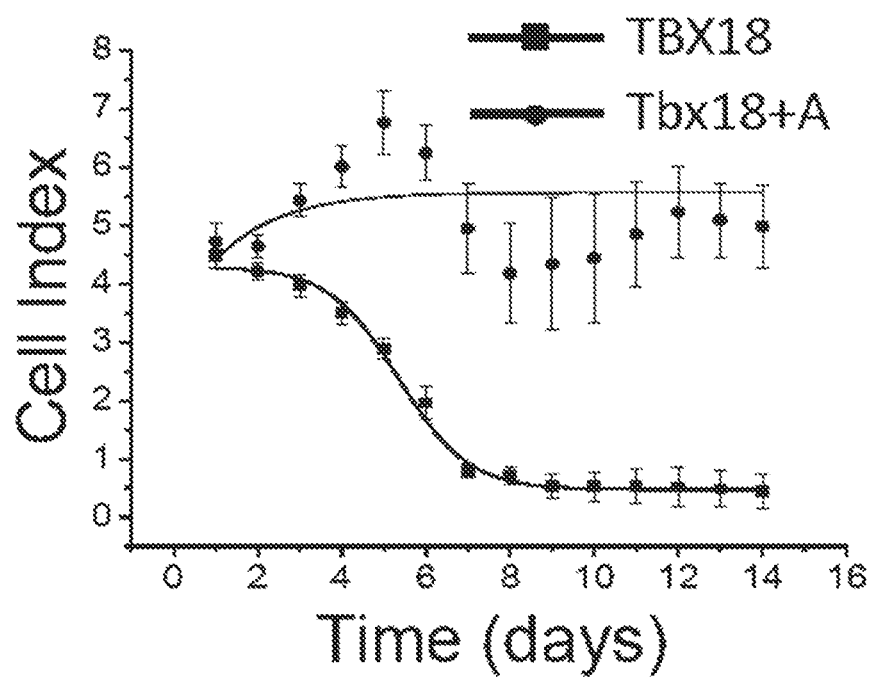
FIG. 2 shows data on electrode-to-electrode impedance measurements indicating TBX18-induced iPCs migrate, but remain stationary upon EMT inhibition. TBX18-iPCs were created by transducing freshly isolated neonatal rat ventricular myocytes (NRVM) with an adenoviral vector expressing human TBX18. TBX18-iPC were cultured with an inhibitor of EMT, A83-01 (0.5 microM).
Figure 3A:
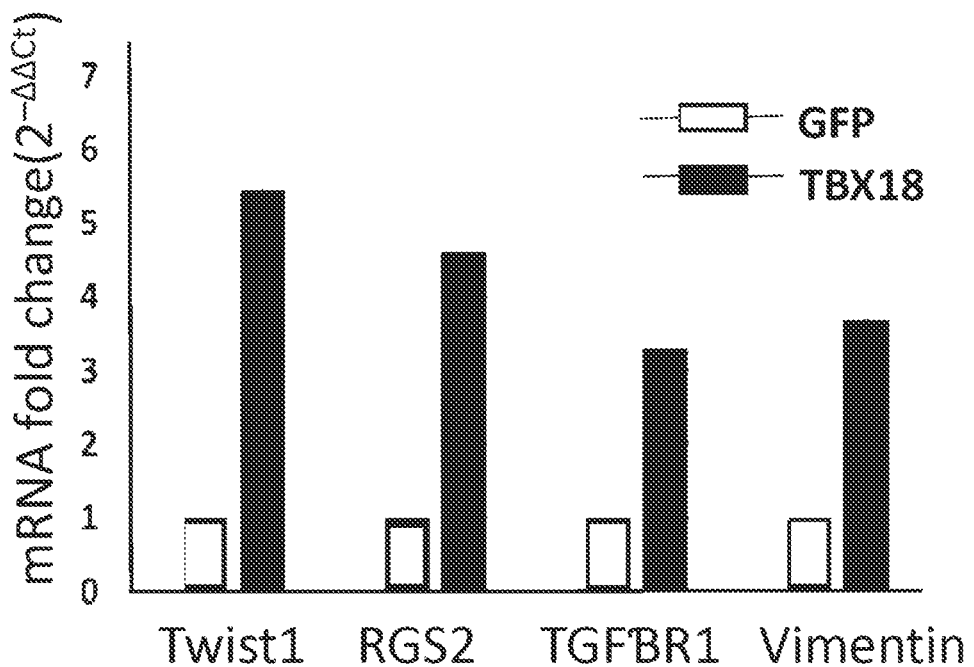
FIG. 3A shows data indicating EMT-related gene expression is upregulated in TBX18-induced pacemaker cells.
Figure 3B:
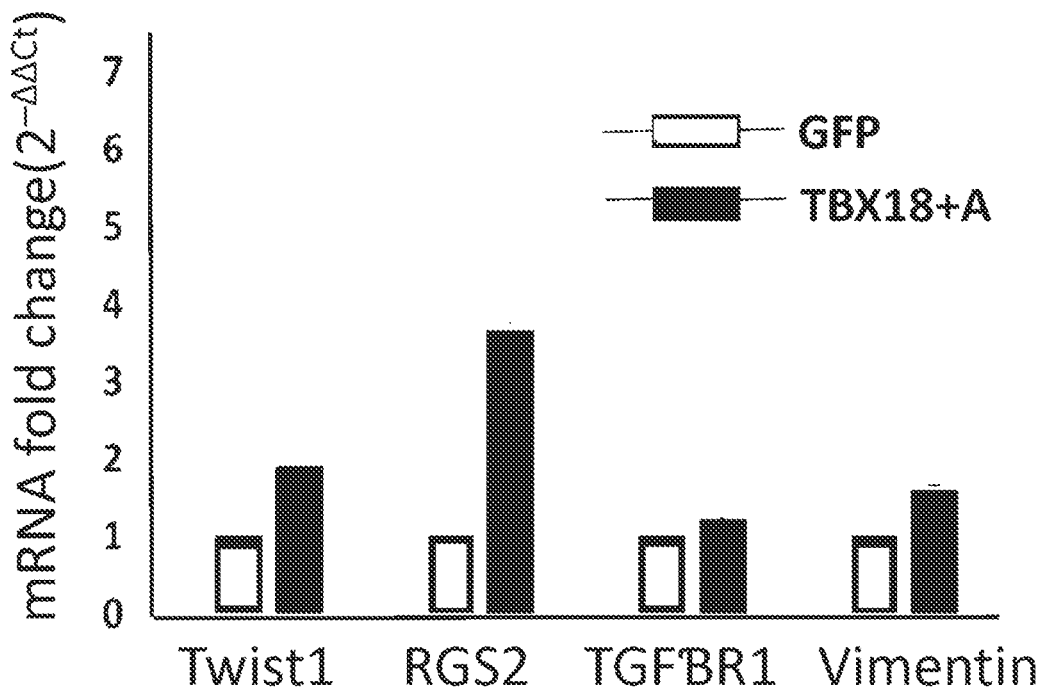
FIG. 3B shows data indication an EMT inhibitor, A83-01, down-regulates EMT genes in the iPCs.
Figure 4A:
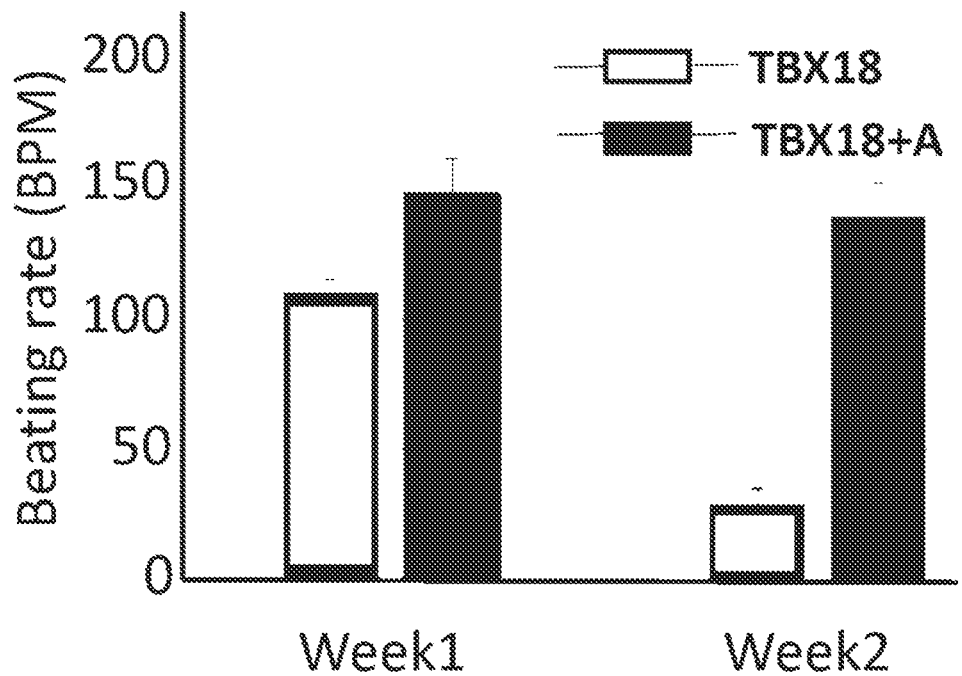
FIG. 4A shows data indicating TBX18-iPCs beating rate increases upon EMT inhibition, and their automaticity persists over long-term.
Figure 4B:
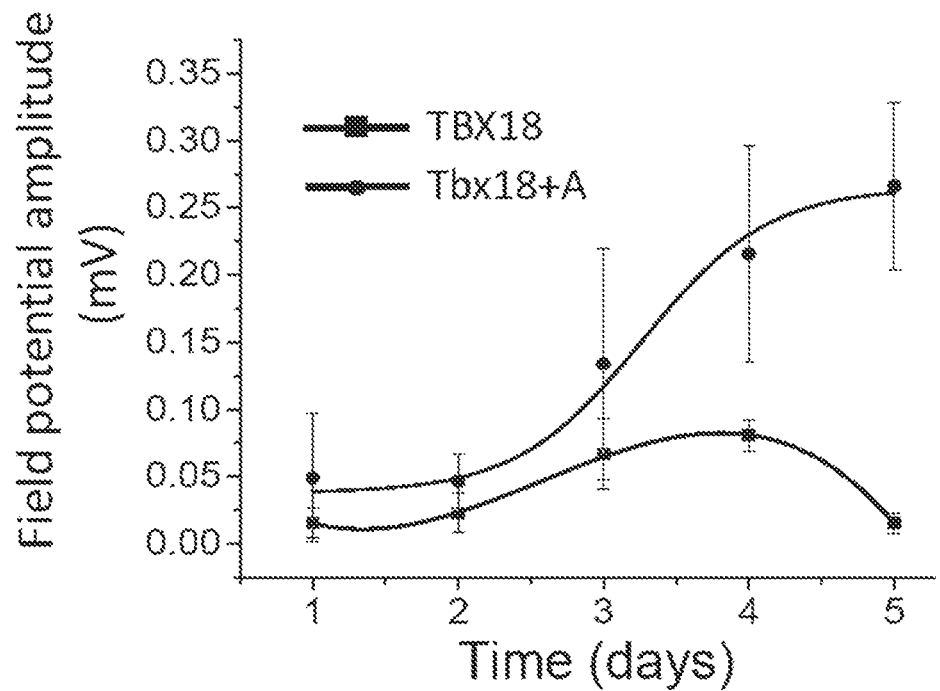
FIG. 4B shows data of a higher field potential amplitude is in TBX18+A as an indication of more TBX18-iPCs beating synchronously upon EMT inhibition.
Figure 7:
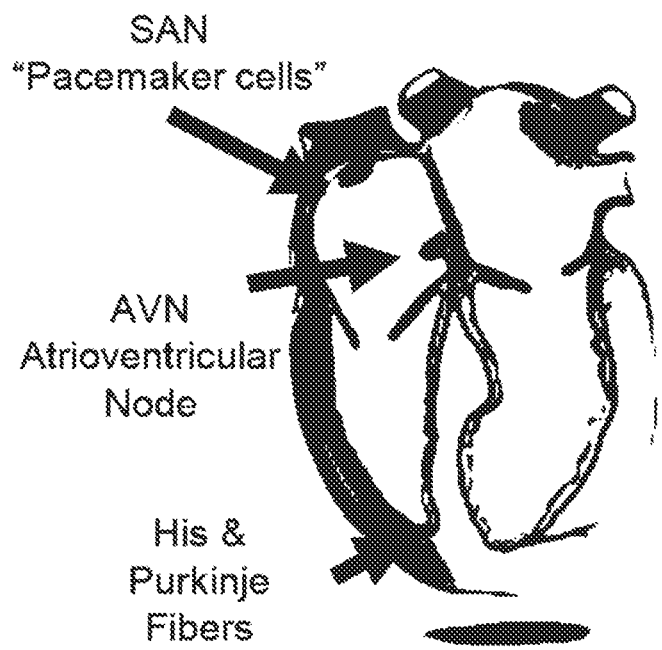
FIG. 7 illustrates the area of SAN pacemaker cells, AVN Atrioventricular Node, and His & Purkinje Fibers.
Figure 8:
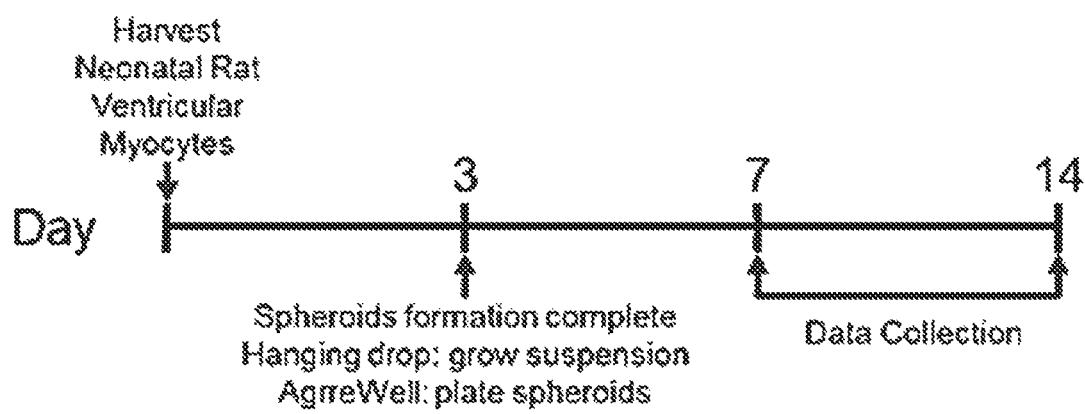
FIG. 8 illustrates an experiment reported herein. The iPCs were created by adenoviral gene transfer of TBX18 to neonatal rat ventricular myocytes. The control group consisted of the same cells transduced with a GFP vector. TBX18 or GFP spheroids were created by exploiting the self-assembling properties of the cardiac myocytes and subjecting them to hanging drops (1000 iPCs/drop). The spheroids were allowed to mature in suspension for one week.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

In certain embodiments, the biological pacemaker consists of a gene, human T-box 18 (TBX18), and a small molecule inhibitor of a cellular pathway called epithelial-to-mesenchymal transformation (EMT). The Tbx18 gene expresses a T-box transcription factor 18. The *Homo sapiens* reference protein can be found on the NCBI national database with accession number NP_001073977 XP_496819, version NP_001073977.1. In certain embodiments, the use of functional variants, allelic variants, or active fragments are contemplated.

An example small molecule inhibitor of EMT is A83-01 with the chemical name, is 3-(6-methyl-2-pyridinyl)-N-phenyl-4-(4-quinolinyl)-1H-pyrazole-1-carbothioamide. There are a number of small molecule inhibitors of EMT such as SB431542 [4-(4-(benzo[d][1,3]dioxol-5-yl)-5-(pyridin-2-yl)-1H-imidazol-2-yl)benzamide], methacycline [(4S, 4aR,5 S,5aR,12aR)-4-(dimethylamino)-1,5,10,11,12a-pentahydroxy-6-methylidene-3,12-dioxo-4,4a, 5,5a-tetrahydrotetracene-2-carboxamide], peaoniflorin, tanshinone IIA [1,6,6-trimethyl-8,9-dihydro-7H-naphtho[1,2-g][1]benzofuran-10,11-dione] See Xi et al. Am J Respir Cell Mol Biol. 2014, 50(1):51-60, Ji et al., Acta Pharmacol Sin. 2016, 37(6):794-804, Tang et al. J Surg Res. 2015, 197(1):167-75. In certain embodiments, the EMT inhibitor is aspirin (acetylsalicylic acid), curcumin, mocetinostat, zidovudine, evodiamine, pyrinium, moscatilin, metformin, palbociclib, icaritin, disulfiram, zerumbone, bufalin, derivatives or salts thereof. In certain embodiments, this disclosure contemplates that any of the epithelial-to-mesenchymal transformation (EMT) inhibitors disclosed herein, salts, or derivatives can be used in any of the method reported herein.

As used herein, the term "derivative" refers to a structurally similar compound that retains sufficient functional attributes of the identified analogue. The derivative may be structurally similar because it is lacking one or more atoms, e.g., replacing an amino group, hydroxyl, or thiol group with a hydrogen, substituted, a salt, in different hydration/oxidation states, or because one or more atoms within the molecule are switched, such as, but not limited to, replacing a oxygen atom with a sulfur atom or replacing an amino group with a hydroxyl group. The derivative may be a prodrug, comprise a lipid, polyethylene glycol, saccharide, polysaccharide. A derivative may compound disclosed herein substituted with one or more substituents. Derivatives may be prepared by any variety of synthetic methods or appropriate adaptations presented in synthetic or organic chemistry textbooks, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, and heteroarylalkyl. The substituents may further optionally be substituted.

Variants of a polypeptide may include 1 or 2 amino acid substitutions or conserved substitutions. Variants may include 3 or 4 amino acid substitutions or conserved substitutions. Variants may include 5 or 6 or more amino acid substitutions or conserved substitutions. Variant include those wherein not more than 1% or 2% of the amino acids are substituted. Variant include those wherein not more than 3% or 4% of the amino acids are substituted. Variants include proteins with greater than 80%, 89%, 90%, 95%, 98%, or 99% identity or similarity. Variants can be tested by mutating a vector to produce appropriate codon alternatives for polypeptide translation. Active variants and fragments can be identified with a high probability using computer modeling. Shihab et al. report an online genome tolerance browser. BMC Bioinformatics. 2017, 18(1):20. Ng et al. report methods of predicting the effects of amino acid substitutions on protein function. Annu Rev Genomics Hum Genet. 2006, 7:61-80. Teng et al. Approaches and resources for prediction of the effects of non-synonymous single nucleotide polymorphism on protein function and interactions. Curr Pharm Biotechnol. 2008, 9(2):123-33.

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic-A V I L; Charged positive: R K H; Charged negative—D E; Polar—S T N Q. The amino acid groups are also considered conserved substitutions.

"Subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

A "heterologous" nucleic acid sequence or peptide sequence refers to a nucleic acid sequence or peptide sequence that do not naturally occur, e.g., because the whole sequences contain a segment from other plants, bacteria, viruses, other organisms, or joinder of two sequences that occur the same organism but are joined together in a manner that does not naturally occur in the same organism or any natural state As used herein a "stem cell" refers to a cell, under certain physiologic or experimental conditions, that can be induced to become tissue- or organ-specific cells with special functions. Stem cell types include embryonic stem cells, adult stem cells, and induced pluripotent stem cells. An adult stem cell or somatic cell is found among differentiated cells in a tissue or organ and can renew itself. Adult stem cells can differentiate to yield some or all of the major specialized cell types of the tissue or organ. Examples of adult stem cells include MSCs. Induced pluripotent stem cells are cells that have been naturally differentiated but exposed to chemicals and/or biologic materials in vitro (treated with reprogramming factors) that allow the cell to differentiate into a larger capacity of specialized cells.

The term "mesenchymal stromal cells" refers to the subpopulation of fibroblast or fibroblast-like nonhematopoietic cells with properties of plastic adherence and capable of in vitro differentiation into cells of mesodermal origin which may be derived from bone marrow, adipose tissue, umbilical cord (Wharton's jelly), umbilical cord perivascular cells, umbilical cord blood, amniotic fluid, placenta, skin, dental pulp, breast milk, and synovial membrane, e.g., fibroblasts or fibroblast-like cells with a clonogenic capacity that can differentiate into several cells of mesodermal origin, such as adipocytes, osteoblasts, chondrocytes, skeletal myocytes, or visceral stromal cells. The term, "mesenchymal stem cells" refers to the cultured (self-renewed) progeny of primary mesenchymal stromal cell populations.

Bone marrow derived mesenchymal stromal cells are typically expanded ex vivo from bone marrow aspirates to confluence. Certain mesenchymal stromal/stem cells share a similar set of core markers and properties. Certain mesenchymal stromal/stem cells may be defined as positive for CD105, CD73, and CD90 and negative or low for CD45, CD34, CD14, and have the ability to adhere to plastic. See Dominici et al. Minimal criteria for defining multipotent mesenchymal stromal cells. The International Society for Cellular Therapy position statement. Cytotherapy, 2006, 8(4):315-7.

Adipose tissue-derived multipotent stem cells (ADMSCs) are multipotent, undifferentiated, self-renewing progenitor cell population isolated from adipose tissue. One method to isolate ADSCs from fat tissue relies on a collagenase digestion, followed by centrifugal density gradient separation. In vitro, ADMSCs typically display a spindle-shaped morphology and lack the intracellular lipid droplets as seen in adipocytes. Isolated ADMSCs are typically expanded in monolayer cultures with a growth medium containing fetal bovine serum and/or human platelet lysate. ADMSCs have the stem cell-specific surface markers, such as CD90, CD105, CD73, and lack the expression of the hematopoietic markers CD45 and CD34.

A Method to Generate Synchronous Pacing from Gene-Induced Biological Pacemakers

An array of diseases can cause the heart to beat too slowly. Bradycardia, also known as bradyarrhythmia or cardiac arrhythmia, is a slow heart rate, defined as a heart rate of under 60 beats per minute (BPM) in adults. Bradycardia typically does not cause symptoms until the rate drops below 50 BPM. When symptomatic, it may cause fatigue, weakness, dizziness, and at very low rates, fainting. During sleep, a slow heartbeat with rates around 40-50 BPM is common, and is considered normal. In general, two types of problems result in bradycardias: disorders of the sinoatrial node (SA node), and disorders of the atrioventricular node (AV node). With sinus node dysfunction (sometimes called sick sinus syndrome), there may be disordered automaticity or impaired conduction of the impulse from the sinus node into the surrounding atrial tissue (an "exit block").

Artificial approaches to pace the heart typically rely on implantable electronic devices otherwise known as pacemakers. The disclosure relates to biological pacemakers for cardiac pacing in patients with abnormally slow heart rhythm. Natural heartbeats originate from the native pacemaker cells. The vast majority of the heart cells have no ability to pace. An array of diseases can cause the heart to beat too slowly, which leads to implantation of electronic cardiac pacing devices. Completely free from all hardware, biological pacemakers consist of a gene and a small molecule, and can convert ordinary muscle cells of the heart to genuine pacemaker cells, unleashing synchronous and rhythmic pacing similar to the native pacemaker tissue.

Experiments disclosed herein indicate that using an EMT inhibitor in combination with TBX18 expression has a number of advantages. Induced cardiac pacemaker cells (iPMs) pace in unity in the presence of A83-01, but not without it. The native pacemaker cells pace in synchrony; and parallel expression of TBX18 and inhibition of EMT recapitulate this. The iPMs' ability to beat on their own, i.e., automaticity, persists much longer in A83-01 than without it. Thus, long-term and/or permanent biological pacing can be achieved. The iPMs' inherent migratory behavior is deleted by blocking EMT with A83-01. This diminishes arrhythmogenic concerns of creating de novo pacemaker cells in the heart.

Noting that the sinus rhythm originates from a unified automaticity of the sinoatrial node (SAN) rather than the individual pacemaker cells, a 3-dimensional ensemble of TBX18-induced pacemaker cells (iPCs) were prepared and tested in comparison to scattered single iPCs in pacing and driving the neighboring myocardium. Developing pacing node by growing cells is able to pace and drive the neighboring myocardium if injected in a heart Gene Delivery, Nucleic Acids, and Vectors Reprogramming cardiomyocytes is accomplished, in several embodiments disclosed herein, by using gene delivery as a means of delivering exogenous genetic material to somatic cells, cardiomyocytes, stem cells, or combinations thereof. In several embodiments, polynucleotides are administered in a nucleic acid delivery system or recombinant vector. In several embodiments, a nucleic acid delivery system comprises a non-viral vector linked to the polynucleotide. Examples of such non-viral vectors include the polynucleotide alone (e.g., naked or synthetically altered nucleic acid e.g, DNA or RNA) or the polynucleotide in combination with a suitable protein, polysaccharide or lipid formulation.

Also contemplated is in vivo delivery of in vitro transcribed mRNA or synthetically modified RNA, or non-naturally occurring RNA encoding transcription factors disclosed herein. See Sahin et al. Nature Reviews Drug Discovery, 13, 759-780 (2014). The mRNA may be non-naturally occurring because 5' and/or 3' UTR regions are modified with mutations to increase the stability of RNA and/or increase the speed of translation and/or contains synthetic modifications, e.g., mRNA containing a phosphorothioate-modified cap. The RNA may be chimeric, e.g., alternate codons or viral 5'- and 3'-UTRs that enhance the stability and translational efficiency of mRNA. In certain embodiments, the mRNA may be mixed and administered in combination with charge-altering releasable transporters (CARTs) or ester polymers comprising monomers with lipid groups and monomers with amine or guanidine groups. See e.g., McKinlay et al. Charge-altering releasable transporters (CARTs) for the delivery and release of mRNA in living animals, PNAS, 2017, 114(4):E448-E456.

Recombinant viral genomes are typically edited so that vectors are non-infectious and replication defective. In certain embodiments, the recombinant vector is capable of stably integrating into a genome of dividing cardiac cells. Lentiviral vectors are capable integrating into a cell genome. In certain embodiments, lentiviral vectors (LVs) comprises promoters including: α-myosin heavy chain (α-MHC), myosin light chain (MLC2v), and cardiac troponin T (cTnT). See Lee et al. Promoter-specific lentivectors for long-term, cardiac-directed therapy of Fabry disease. J Cardiol. 2011, 57(1):115-22.

In several embodiments, the recombinant vector comprise one or more viral sequences, including but not limited to adenovirus, adenovirus-associated virus (AAV), helper-dependent adenovirus, lentivirus, retrovirus, or hemaglutinating virus of Japan-liposome (HVJ) complex. Various serotypes of adenovirus and/or AAV are also used in several embodiments. In several embodiments, the viral vector comprises a eukaryotic promoter. In several embodiments, cytomegalovirus (CMV) promoters are used. Other promoters, including tissue-specific promoters may be used in certain embodiments. Additional vectors include retroviral vectors such as moloney murine leukemia viruses and lentiviruses. In one embodiment, a lentiviruses vector comprises at least two vectors wherein the gag and pol genes are from an HIV genome and the env gene is from another virus. DNA viral vectors are used in some embodiments, which include, but are not limited to pox vectors such as orthopox or avipox vectors, herpes virus vectors such as a herpes simplex I virus (HSV) vector.

In several embodiments, polynucleotides (e.g. those encoding one or more transcription factors) are administered in vivo and/or in vitro to convert cells (stem, cardiomyocytes, and/or other somatic cells) into pacemaker cells. In some embodiments, polynucleotides that encode a functional fragment of the transcription factor are delivered in addition to, or in place, of the entire transcription factor. As used herein, the terms "fragment", "functional fragment" or similar terms shall be given their ordinary meaning and shall refer to a portion of an amino acid sequence (or polynucleotide encoding that sequence) that has at least about 70%, preferably at least about 80%, more preferably at least about 90%, 95%, 96%, 97%, 98% or 99% of the function of the corresponding full-length amino acid sequence (or polynucleotide encoding that sequence). Methods of detecting and quantifying functionality of such fragments are established in the art.

Thus, in certain embodiments, the disclosure contemplates recombinant nucleic acids vectors and cells comprising the same. In certain embodiments, the disclosure relates to expression systems comprising a nucleic acid encoding a transcription factor such as a recombinant vector comprising a nucleic acid encoding transcription factor disclosed herein such as Tbx18. In certain embodiments, the disclosure relates to cells comprising a nucleic acid encoding a transcription factor such as a recombinant vector comprising a nucleic acid encoding transcription factor disclosed herein. In certain embodiments, the disclosure relates to a vector comprising the nucleic acid encoding a transcription factor disclosed herein and a heterologous nucleic acid sequence.

The terms "recombinant vector" refers to a recombinant nucleic acid containing a desired coding sequence and appropriate nucleic acid sequences necessary for the expression of the operably linked coding sequence in particular cells A "selectable marker" is a nucleic acid introduced into a nucleic acid encoding a transcription factor such as a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme that confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferasel (galT), feedback-insensitive a subunit of anthranilate synthase (OASA1D), 2-deoxyglucose (2-DOGR), benzyladenine-N-3-glucuronide, E. coli threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as 35S or 131I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the disclosure relates to the recombinant vectors comprising a nucleic acid encoding a transcription factor disclosed herein or fusion protein thereof. In certain embodiments, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

In certain embodiments, the disclosure relates to a nucleic acid encoding a transcription factor disclosed herein wherein the nucleotide sequence has been changed to contain at least one non-naturally occurring substitution and/or modification relative to the naturally occurring sequence, e.g., one or more nucleotides have been changed relative to the natural sequence. In certain embodiments, the disclosure relates to a nucleic acid encoding a transcription factor disclosed herein further comprising a label.

Delivery Methods

In several embodiments, administration of the compositions (being nucleic acids encoding transcription factors or cells) disclosed herein to modulate cardiac electrical activity is via direct cardiac injection (e.g., during electronic pacemaker implantation or explantation). In some embodiments, systemic injection is used. Intracoronary injection is used in some embodiments. In still additional embodiments, catheter-directed administration is used. In some embodiments, a map-guided catheter system (e.g., NOGA™) is used in order to focally administer the compositions. Other mapping or guidance techniques are used in some embodiments. For example, in several embodiments fluoroscopy-based guidance is used. Electroanatomical guidance is also used in some embodiments. Mapping of specific structures (including but not limited to the His Bundle, the right or left portions of the bundle, the Purkinje fibers, etc) by intracardiac electrograms are also used in some embodiments. Moreover, X-rays or magnetic catheters are also used in some embodiments to guide delivery of a catheter, needle, or other delivery device(s) to a desired target location.

In several embodiments, a focal delivery approach advantageously reduces the time to generation of an active biological pacemaker. In some embodiments, the tissue-specific (or cell type-specific) delivery of several of the constructs disclosed herein is advantageous in that the construct is particularly suited for facilitating the generation of a biological pacemaker based on the expression profile of endogenous tissues. In some such embodiments, combinations of transcription factors are delivered to the same target site, while in other embodiments, individual constructs are delivered to distinct target sites, with the overall effect resulting in biological pacemaker generation.

In several embodiments, transduction is achieved by focal injection into the apex of the heart. In several embodiments, transduction is achieved by focal injection to the left ventricular apex. In several embodiments, a right-sided (e.g., right side of the heart, either atrium or ventricle) approach is used, in order to reduce the risk of stroke or other embolism. However, in several embodiments, left-sided approaches are used. In several embodiments, an injection catheter is introduced via the right atrium (rather than the right ventricle), in order to access the Bundle of His or AV node from above. In several embodiments, trans-septal catheter methods are used to introduce an injection catheter into the left atrium or left ventricle without the need for arterial access, thereby reducing stroke risk. In still additional embodiments, the introduction of an injection catheter is by way of the cardiac veins via the sinus of Valsalva for injection of a biologic as disclosed herein into various targets of the ventricles. Such an approach is similar to that used for the placement of pacer leads in cardiac resynchronization therapy.

Thus, in several embodiments, the compositions as disclosed herein can be used to deliver one or more transcription factors (or cells that have been previously contacted with the transcription factors) to either the right atrium, right ventricle, SA node, AV node, bundle of his, and/or left and right bundle branches. Moreover, through cannulation of the coronary sinus and its venous branches delivery to multiple left ventricular sites is achieved in several embodiments. Advantageously, in those patients with unfavorable coronary venous anatomy, access to the left side is achieved, in several embodiments, from the right side through a trans-septal puncture which allows direct access to left sided structures without the need of arterial access.

Supplemental methods are used in several embodiments and include administration of compounds to increase the microvascular permeability of the cardiac tissue. Suitable vascular permeability agents (administered prior to, during, or after administration of a gene transfer vector) include a solution having less than about 500 micromolar calcium: substance P, histamine, acetylcholine, an adenosine nucleotide, arachidonic acid, bradykinin, endothelin, endotoxin, interleukin-2, nitroglycerin, nitric oxide, nitroprusside, a leukotriene, an oxygen radical, phospholipase, platelet activating factor, protamine, serotonin, tumor necrosis factor, vascular endothelial growth factor, a venom, a vasoactive amine, or a nitric oxide synthase inhibitor, serotonin, vascular endothelial growth factor (VEGF), or a functional VEGF fragment.

Biological Pacemaker Effect on Tissues

In several embodiments, administration of transcription factors (or cells contacted with those transcription factors in vitro) disclosed herein induces or otherwise causes the spontaneous repetitive electrical signals to be generated in cells that previously responded to such signals, but did not generate them. For example, for treated myocardial cells that exhibited little (e.g., an index of automaticity between about 40% to about 30%, about 30% to about 20%, about 20% to about 10%, or about 10% to about 0%, or overlapping ranges thereof) or no firing rate, exhibit an increased frequency of firing rate or electrical signal output post-administration (e.g., an index of automaticity of between about 5% to about 15%, about 15% to about 25%, about 25% to about 35%, about 35% to about 45%, about 45% to about 55%, about 55% to about 65%, about 65% to about 75%, about 75% to about 85%, about 85% to about 95%, about 95% to about 100%, or more) as compared to the cells pre-administration.

The resultant changes in cardiac contraction and/or an electrical property of converted pacemaker cells, by the methods disclosed herein, modulate cardiac rhythm in several embodiments. In several embodiments, the methods and compositions disclosed herein achieve a heart rate within about 25%, within about 20%, within about 15%, within about 10%, within about 5%, within about 2%, or within about 1% of a clinically desired heart rate. In several embodiments, the methods and compositions disclosed herein are used to treat subjects suffering from or susceptible to a disease or disorder such as a cardiac-related syncope (e.g., Stokes-Adam syncope), an abnormality of sinus node function such as persistent sinus bradycardia, sino-atrial (S-A) block manifested as S-A Wenckebach, complete S-A block or sinus arrest, and high-grade atrioventricular block; or bradycardia-tachycardia syndrome or other bradycardia related condition. In several embodiments, modulation is used to increase or slow down the function of an implanted pacemaker (e.g., to achieve a desired heart rate that the implanted pacemaker fails to provide on its own).

Changes to the Cells

In several embodiments, the administration of an epithelial-to-mesenchymal transformation inhibitor in combination with a transcription factor or a nucleic acid encoding the same such as Tbx18 produces several physiological changes to the contacted cells in addition to or separate from the generation of spontaneous repetitive electrical signals discussed above. In some embodiments, these physiological changes even if first seen in vitro, are also detectable in vivo, where they may serve as supplemental markers of the efficacy of biological pacemaker generation (e.g., they are recognized as characteristics or hallmarks of pacemaker cells). In some embodiments, the administration of one or more transcription factors or a nucleic acid encoding the same results in an increased percentage of spontaneously beating monolayer cultures or spherical aggregates compared to control. In several embodiments, the presence, or amount, of spontaneous beating is use to screen cultures for functionality prior to transplant or to evaluate other combinations of transcription factors for their utility in generating pacemaker cells in vitro.

In some embodiments, the administration of one or more transcription factors or a nucleic acid encoding the same results in spontaneous intracellular $Ca^{2+}$ oscillations of myocardial cells are administered. In some embodiments, the administration of one or more transcription factors or a nucleic acid encoding the same results in a gradual phase-4 depolarization. In some embodiments, the delivery of one or more transcription factors or a nucleic acid encoding the same disclosed herein increases or decreases the expression of HCN4 in cells. Because calcium flux is a primary component of cardiac electrical signaling and HCN4 expression is important in pacemaker cell function, changes in these endpoints correspond, in some embodiments, to more SAN-like behavior in induced biological pacemaker cells. In some embodiments, the administration of one or more transcription factors or a nucleic acid encoding the same results in modulation of sub-sarcolemmal, spontaneous localized $Ca^{2+}$ release events. In some embodiments, the administration of one or more transcription factors or a nucleic acid encoding the same results in modulation of intracellular cAMP levels. Thus, as a result of administration of one or more of the above types of transcription factors or a nucleic acid encoding the same, cardiac electrical activity can be modulated and abnormalities in excitable cardiac tissue can be treated.

In several embodiments, the administration of an epithelial-to-mesenchymal transformation inhibitor in combination with Tbx18, Shox2, or a combination thereof or a nucleic acid encoding the same will result in cells new phenotypes of the contacted cells in addition to or separate from the generation of spontaneous repetitive electrical signals. In some embodiments, the administration of an epithelial-to-mesenchymal transformation inhibitor and one or more transcription factors or a nucleic acid encoding the same results in disorganized and markedly lower sarcomeric alpha-actin expression in transduced cells, which is indicative of pacemaker cells. In some embodiments, the administration of an epithelial-to-mesenchymal transformation inhibitor and one or more transcription factors or a nucleic acid encoding the same results in a change in cell size. In some embodiments, the administration of an epithelial-to-mesenchymal transformation inhibitor and one or more transcription factors or a nucleic acid encoding the same results in changes to the chromatin state. In some embodiments, the administration of an epithelial-to-mesenchymal transformation inhibitor and one or more transcription factors or a nucleic acid encoding the same results in chromatin modification and will cause lower or higher expression and or activity of one or more of the following genes: Cx43, Kir2.1, Actc2, and HCN4. These phenotypic changes, mirror those of natural SAN cells and as a result of the administration of an epithelial-to-mesenchymal transformation inhibitor and one or more of these transcription factors or a nucleic acid encoding the same, can be used, in several embodiments, as an additional means to evaluate the generation of biological pacemaker cells.

In several embodiments, the administration of an epithelial-to-mesenchymal transformation inhibitor and one or more transcription factors or a nucleic acid encoding the same to the heart will result in frequent ectopic ventricular beats that originate from the site of gene injection resulting in targeted generation of pacemaker activity. In some embodiments, the administration of an epithelial-to-mesenchymal transformation inhibitor and one or more transcription factors or a nucleic acid encoding the same results in gene-related epigenetic changes in cells and de novo pacemaker activity. This pacemaker activity, in some embodiments, is a result of somatic reprogramming, and not due to dedifferentiation to a progenitor state. Somatic to somatic transdifferentiation will lower the threat of neoplasia from transduced cells (e.g., teratoma formation is reduced). In other embodiments, however, the administration of an epithelial-to-mesenchymal transformation inhibitor and one or more transcription factors or a nucleic acid encoding the same may result in dedifferentiation to a progenitor state. In certain such embodiments, differentiation into pacemaker cells is induced using one or more of the transcription factors disclosed herein. Using such methods, biological pacemaker cells can effectively be made from a wide variety of cells.

Pharmaceutical Compositions

In certain embodiments, the disclosure relates to a pharmaceutical composition comprising an epithelial-to-mesenchymal transformation inhibitor disclosed herein such as 3-(6-methyl-2-pyridinyl)-N-phenyl-4-(4-quinolinyl)-1H-pyrazole-1-carbothioamide or salts thereof and a pharmaceutically acceptable excipient. In certain embodiments, the composition further comprises one or more transcription factors or a nucleic acid encoding a transcription factor such as a recombinant vector that encodes a transcription factor such as Tbx18 in operable combination with a eukaryotic promoter In certain embodiments, the pharmaceutical composition is in the form of a sterilized pH buffered aqueous salt solution or a saline phosphate buffer between a pH of 6 to 8, optionally comprising a saccharide or polysaccharide.

In certain embodiments, the pharmaceutical composition is in the form of a tablet, pill, capsule, gel, gel capsule, or cream. In certain embodiments, the pharmaceutically acceptable excipient is a solubilizing agent selected from a lipid, cholesterol, fatty acid, fatty acid alkyl ester, linoleic acid, oleic acid arachidonic acid, saccharide, polysaccharide, cyclodextrin, 2-hydoxypropyl(cyclodextrin), or combinations thereof.

In certain embodiments, the pharmaceutically acceptable excipient is selected from lactose, sucrose, mannitol, triethyl citrate, dextrose, cellulose, methyl cellulose, ethyl cellulose, hydroxyl propyl cellulose, hydroxypropyl methylcellulose, carboxymethylcellulose, croscarmellose sodium, polyvinyl N-pyrrolidone, crospovidone, ethyl cellulose, povidone, methyl and ethyl acrylate copolymer, polyethylene glycol, fatty acid esters of sorbitol, lauryl sulfate, gelatin, glycerin, glyceryl monooleate, silicon dioxide, titanuium dioxide, talc, corn starch, carnuba wax, stearic acid, sorbic acid, magnesium stearate, calcium stearate, castor oil, mineral oil, calcium phosphate, starch, carboxymethyl ether of starch, iron oxide, triacetin, acacia gum, esters, or salts thereof.

Examples

EMT Inhibition Unleashes Synchronous and Rhythmic Pacing from TBX18-Induced Pacemaker Cells The heartbeat originates from the sinoatrial node (SAN). Conversion of ordinary, quiescent cardiomyocytes to induced pacemaker cells (iPCs) can be accomplished by a re expression of Tbx18. However, the iPCs cease to beat synchronously over time, unable to output a singular rhythm. Tbx18 is known to play two anatomically distinct roles, one specifying the SAN development and the other mediating epithelial-to-mesenchymal transition (EMT). EMT is known to initiate migratory behavior, which could run counter to the pacemaker cells' task to pace-and-drive.

Experiments were performed to test whether i) TBX18-induced pacemaker cells (TBX18-iPCs) migrate, and ii) inhibition of EMT in TBX18-iPCs may stop the migration, thereby enhancing its pacing function. (See FIGS. 1-8). TBX18-iPCs were created by transducing freshly-isolated neonatal rat ventricular myocytes (NRVM) with an adenoviral vector expressing human TBX18. TBX18-iPC were cultured with an inhibitor of EMT, A83-01. Data indicates that TBX18-induced iPCs migrate, but remain stationary upon EMT inhibition. EMT-related gene expression is upregulated in TBX18-induced pacemaker cells. An EMT inhibitor, A83-01, down-regulates EMT genes in the iPCs. TBX18-iPCs beat in synchrony upon EMT inhibition, and their automaticity persists over long-term. TBX18-iPCs contract and relax faster upon EMT inhibition. TBX18-iPCs exhibit synchronous and rhythmic pacing upon EMT inhibition, resembling that of the native sinoatrial node tissue. Nuclear-bound Cx43 proteins in TBX18-iPCs become translocated to the sarcolemma upon EMT inhibition. EMT inhibition enhances Hcn4 expression in TBX18-iPCs.

TBX18 mediates both automaticity and EMT in iPCs. EMT blockade creates synchronous and rhythmic pacing from TBX18-iPCs, similar to the native SAN. EMT-inhibited TBX18-iPCs show long-term gap junctional coupling, and higher levels of HCN4 transcripts and proteins. Engineered Biological Pacing Nodes Created from Induced Pacemaker Cells Transformation of ordinary cardiac myocytes to pacemaker cells can be accomplished by a transient expression of TBX18. Noting that the sinus rhythm originates from a unified automaticity of the sinoatrial node (SAN) rather than the individual pacemaker cells, a 3-dimensional ensemble of TBX18-induced pacemaker cells (iPCs) is desirable for pacing and driving the neighboring myocardium.

The iPCs were created by adenoviral gene transfer of TBX18 to neonatal rat ventricular myocytes. The control group consisted of the same cells transduced with a green fluorescent protein (GFP) vector. TBX18 or GFP spheroids were created by exploiting the self-assembling properties of the cardiac myocytes and subjecting them to hanging drops (1000 iPCs/drop). The spheroids were allowed to mature in suspension for one week.

Three weeks after the spheroid formation, TBX18 spheroids maintained spontaneous pacing at 100±4 bpm while GFP spheroids were rarely active (0.01±0.01 bpm, p=0.0106). Monolayers of TBX18 cells exhibited automaticity, but such automaticity were often asynchronous, and the monolayers ceased to be viable in <2 weeks. Reflecting the weak electrical coupling in the SA node, the conduction velocity of TBX18 spheroids (1.3±0.9 cm/s) was 15-fold lower than that of GFP spheroids (19±12 cm/s). The slow conduction velocity in TBX18 spheroids was attributed to 17-fold increase in a small conductance gap junction, Cx45, transcripts ($p<0.0001$) and a 2-fold decrease in myocardial gap junction, Cx43 (p=0.003), compared to GFP-spheroids. When a cluster of 15-20 spheroids was surrounded by a monolayer of ventricular myocytes, TBX18, but not GFP, spheroids were able to pace and drive the neighboring sheet of ventricular myocytes. A monolayer of TBX18 cells failed to pace and drive the neighboring sheet of ventricular myocytes at the same source-to-sink ratio.

In Vivo Administration of TBX18 and EMT, A83-01

Figure 9A:
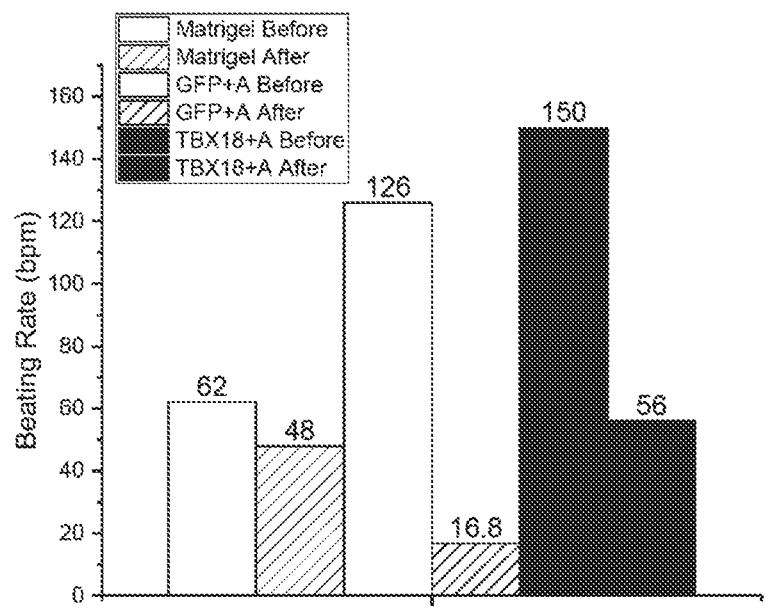
FIG. 9A shows data on beating heart rate for spheroid-like aggregates generated using the process in FIG. 8 and injecting the injection of spheroid-like aggregates with matrigel in a rat heart.
Figure 9B:
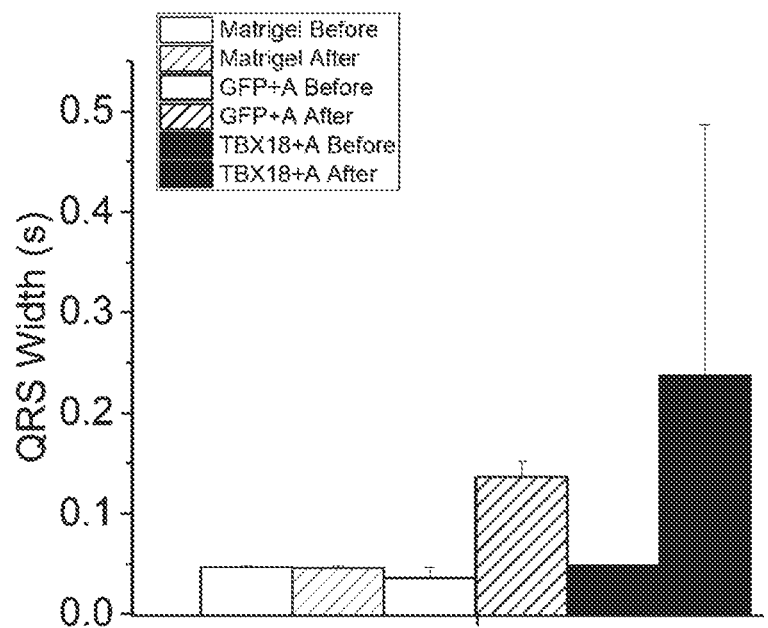
FIG. 9B shows data on for EKG recordings for spheroid-like aggregates generated using the process in FIG. 8 and injecting the injection of spheroid-like aggregates with matrigel in a rat heart.

Rat heart extraction and perfusion setup for EKG recordings was prepared. Spheroidal-like aggregates were prepared with GFP and A83-01 and TBX18 and A83-01. The aggregates in a matrigel where injecting in rat heart apex. Ectopic beats were identified with TBX18 and A83-01 in vivo. (See FIGS. 9A and 9B)

The invention claimed is:

1. A method of treating a heart from beating abnormally comprising implanting an effective amount of spontaneously beating expanded cells into the heart of a subject in need thereof, wherein the spontaneously beating expanded cells are made by a process comprising mixing cardiomyocytes with
   a) an epithelial-to-mesenchymal transformation inhibitor, wherein the epithelial-to-mesenchymal transformation inhibitor is 3-(6-methyl-2-pyridinyl)-N-phenyl-4-(4-quinolinyl)-1H-pyrazole-1-carbothioamide or salt thereof, and
   b) a nucleic acid encoding Tbx18;
   thereby delivering a) and b) into the cardiomyocytes, wherein the cardiomyocytes proliferate after mixing with a) and b), forming spontaneously beating expanded cells.

2. The method of claim 1, wherein the spontaneously beating expanded cells are formed as an aggregate in a hanging droplet.

3. The method of claim 1, wherein the subject is diagnosed with cardiac arrhythmia, sick sinus syndrome, sinus bradycardia, tachycardia-bradycardia syndrome, atrial fibrillation, atrioventricular block, chronotropic incompetence, prolonged QT syndrome, or heart failure.

4. A method of treating or preventing a heart from beating abnormally comprising administering an effective amount of an epithelial-to-mesenchymal transformation inhibitor, wherein the epithelial-to-mesenchymal transformation inhibitor is 3-(6-methyl-2-pyridinyl)-N-phenyl-4-(4-quinolinyl)-1H-pyrazole-1-carbothioamide or salt thereof, in combination with a nucleic acid encoding Tbox18 to a subject in need thereof.

5. The method of claim 4, wherein the nucleic acid is a recombinant vector encoding Tbox18 operably linked to a eukaryotic promoter.

6. The method of claim 4, wherein the subject is diagnosed with cardiac arrhythmia, sick sinus syndrome, sinus bradycardia, tachycardia-bradycardia syndrome, atrial fibrillation, atrioventricular block, chronotropic incompetence, prolonged QT syndrome, or heart failure.

7. The method of claim 4 wherein administering an effective amount of 3-(6-methyl-2-pyridinyl)-N-phenyl-4-(4-quinolinyl)-1H-pyrazole-1-carbothioamide in combination with a nucleic acid encoding Tbox18 further comprises administering one or more nucleic acids encoding Shox2, Tbx3, Tbx5, or combinations thereof.

8. The method of claim 1 wherein mixing cells with a) 3-(6-methyl-2-pyridinyl)-N-phenyl-4-(4-quinolinyl)-1H-pyrazole-1-carbothioamide, and b) a nucleic acid encoding Tbx18, further comprise mixing cells with one or more nucleic acids encoding Shox2, Tbx3, Tbx5, or combinations thereof.

\* \* \* \* \*

UNITED STATES PATENT AND TRADEMARK OFFICE
CERTIFICATE OF CORRECTION

| | | |
|---|---|---|
| PATENT NO. | : 11,371,020 B2 | Page 1 of 1 |
| APPLICATION NO. | : 16/098560 | |
| DATED | : June 28, 2022 | |
| INVENTOR(S) | : Hee Cheol Cho | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 515 days.

Signed and Sealed this
Eleventh Day of February, 2025

Coke Morgan Stewart
*Acting Director of the United States Patent and Trademark Office*